US007530952B2

(12) United States Patent
Huang et al.

(10) Patent No.: US 7,530,952 B2
(45) Date of Patent: May 12, 2009

(54) CAPACITIVE ULTRASONIC TRANSDUCERS WITH ISOLATION POSTS

(75) Inventors: Yongli Huang, San Jose, CA (US); Butrus T. Khuri-Yakub, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 447 days.

(21) Appl. No.: 10/817,381

(22) Filed: Apr. 1, 2004

(65) Prior Publication Data

US 2005/0228285 A1 Oct. 13, 2005

(51) Int. Cl.
*A61B 8/00* (2006.01)
*H04R 19/00* (2006.01)

(52) U.S. Cl. ....................... 600/459; 600/437; 310/324; 367/163; 367/181

(58) Field of Classification Search ................. 600/437, 600/459; 367/163, 174, 181, 189; 310/324, 310/328

See application file for complete search history.

(56) References Cited

U.S. PATENT DOCUMENTS

| | | | | |
|---|---|---|---|---|
| RE28,420 | E * | 5/1975 | Murphy | 307/400 |
| 4,070,741 | A * | 1/1978 | Djuric | 29/25.42 |
| 4,081,626 | A * | 3/1978 | Muggli et al. | 367/181 |
| 4,192,977 | A * | 3/1980 | Stamm | 310/363 |
| 4,418,246 | A * | 11/1983 | Sawyer | 310/300 |
| 4,665,610 | A * | 5/1987 | Barth | 438/53 |
| 5,287,331 | A * | 2/1994 | Schindel et al. | 367/140 |
| 5,619,476 | A * | 4/1997 | Haller et al. | 367/181 |
| 5,946,273 | A * | 8/1999 | Lissel et al. | 367/181 |
| 6,144,481 | A | 11/2000 | Kowarz et al. | |
| 6,328,697 | B1 * | 12/2001 | Fraser | 600/459 |
| 6,388,299 | B1 * | 5/2002 | Kang et al. | 257/415 |
| 6,558,330 | B1 * | 5/2003 | Ayter et al. | 600/459 |
| 2005/0018536 | A1 * | 1/2005 | Caliano et al. | 367/7 |

OTHER PUBLICATIONS

Amjadi, H., et al., "Charge Storage In Double Layers Of Silicon Dioxide And Silicon Nitride", 9th *International Symposium on Electrets*, Sep. 25-30, 1996, pp. 22-27.

Antoniu, A., et al., "Effects of Electrostatic Charge Accumulation During MEMS Fabrication", MEMS, NANO and Smart Systems, 2003. Proceedings. International Conference on Jul. 20-23, 2003, pp. 69-75.

Denatale, J., et al., "RF MEMS Reliability", *The 12th International Conference on Solid State Sensors, Actuators and Microsystems*, Boston, Jun. 8-12, 2003, pp. 943-946.

(Continued)

*Primary Examiner*—Eric F Winakur
(74) *Attorney, Agent, or Firm*—Perkins Coie, LLP

(57) ABSTRACT

A capacitive ultrasonic transducer is described which include one or more cells including a cavity defined by a membrane electrode supported spaced from a support electrode by insulating walls with a patterned isolation layer having isolation posts or areas located in said cavity to prevent the electrodes for coming into contact during operation of the transducer, and to minimize the accumulation of charge as compared to a non-patterned isolation layer for preventing contact of the electrodes during operation of the transducer.

15 Claims, 4 Drawing Sheets

OTHER PUBLICATIONS

Gilbert, J.R., et al., "3D Modeling of Contact Problems and Hysteresis in Coupled Electro-Mechanics", IEEE Annual International Conference on Microelectromechanical Systems, 1996, pp. 127-132.

Goldsmith, C. et al., "Lifetime Characterization Of Capacitive RF MEMS Switches", *Microwave Symposium Digest, 2001 IEEE MTT-S International*, May 20-25, 2001, 1: 227-230.

Huang, Y., et al., "Capacitive Micromachined Ultrasonic Transducers (cMUTS) With Isolation Posts", Presented at the 2004 *IEEE International Ultrasonics Symposium*, Montreal, Canada, Aug. 23-27, 2004.

Huang, Y., et al., "Fabricating Capacitive Micromachined Ultrasonic Transducers With Wafer-Bonding Technology", *Journal of Microelectromechanical Systems*, Apr. 2003, 12(2): 128-137.

Huang, Y., et. al., "A Solution to the Charging Problems in Capacitive Micromachined Ultrasonic Transducers (CMUTS)", accepted for publication, IEEE Trans., *Ultrason., Ferroelect. Freg. Contr.*

Jin, X., et al., "Fabrication and Characterization of Surface Micromachined Capacitive Ultrasonic Immersion Transducers", *IEE Journal of Microelectromechanical Systems*, Mar. 1999, 8(1): 100-114.

Reid, J.R., et al., "Noncontact Measurement of Charge Induced Voltage Shift in Capacitive MEM-Switches", *IEEE Microwave and Wireless Components Letters*, Sep. 2003, 13(9): 367-369.

Shea, H.R., et al., "Effects of Electrical Leakage Currents on MEMS Reliability and Performance", *IEEE Transactions on Device and Materials Reliability*, Jun. 2004, 4(2): 198-207.

Van Spengen, W.M., et al., "Experimental Characterization Of Stiction Due to Charging In RF MEMS", Electron Devices Meeting, 2002. IEDM '02. Digest. International, Dec. 8-11, 2002, pp. 901-904.

Yuan, X., et al., "Initial Observation and Analysis of Dielectric-Charging Effects on RF MEMS Capacitive Switches", Microwave Symposium Digest, 2004 IEEE MTT-S International, Jun. 6-11, 2004, 3(3): 1943-1946.

Yuang, Y., et al., "New Fabrication Process for Capacitive Micromachined Ultrasonic Transducers": 1-4.

* cited by examiner

CAPACITIVE ULTRASONIC TRANSDUCERS WITH ISOLATION POSTS

GOVERNMENT SUPPORT

This invention was made with Government support under Grant No. Navy N00014-02-1-0007 awarded by the Department of the Navy, Office of Naval Research. The Government has certain rights in this invention.

BRIEF DESCRIPTION OF THE INVENTION

This invention relates generally to capacitive micromachined ultrasonic transducers (cMUTs) and more particularly to capacitive micromachined ultrasonic transducers having a patterned isolation layer which prevents shorting of the electrodes during operation and reduces the total number of trapped charges as compared to a non-patterned isolation layer.

BACKGROUND OF THE INVENTION

Ultrasonic transducers have been used in a number of sensing applications such as medical imaging, non-destructive evaluation, gas metering and a number of ultrasound generating application such medical therapy, industrial cleaning, etc. One class of such transducers is the electrostatic transducers. Electrostatic transducers have long been used for receiving and generating acoustic waves. Large area electrostatic transducer arrays have been use for acoustic imaging. The electrostatic transducers employ resilient membranes with very little inertia substrate which forms the second electrode. When distances between the electrodes are small the transducers can exert very large forces against a fluid in contact with the membrane. The momentum carried by approximately half a wavelength of air molecules in contact with the upper surface is able to set the membrane in motion and vice versa. Electrostatic actuation and detection enables the realization and control of such membranes.

Broad band microfabricated capacitive ultrasonic transducers (cMUTs) may include multiple elements each including membranes of identical or different sizes and shapes supported above a silicon substrate by walls of an insulating material which together with the membrane and substrate define cells. The walls are formed by micromachining a layer of insulation material such as silicon oxide, silicon nitride, etc. The substrate can be glass or other substrate material. The capacitive transducer is formed by a conductive layer on the membrane and conductive means such as a layer either applied to the substrate or the substrate having conductive regions. A single cell of a cMUT is illustrated in FIG. 1. The cMUT includes a bottom electrode 11 and a top electrode or membrane 12 supported by insulating walls 13. When suitable AC and DC voltages are applied between the electrodes electrostatic forces cause the membrane to oscillate and generate acoustic waves. Alternately a DC voltage applied between the electrodes can be modulated by oscillation of the membrane resulting from sound waves stricking the membrane. The cMUT includes an isolation layer 14 such as an oxide layer to prevent shorting between the electrodes if the membrane is deflected into contact the bottom wall of the cell 16.

The electric field between the electrodes can attract and trap charges 17 either on the surface of or in the isolation layer 14. The charges stay in the trapping cites for a long period because there is no DC path to discharge them. The accumulated charge shifts the DC voltage between the two electrodes away from the applied voltage by a random value. This dramatically degrades the reliability and repeatability of device performance.

OBJECTS AND SUMMARY OF THE PRESENT INVENTION

It is an object of the present invention to provide cMUTs in which trapped charges are minimized.

It is a further object of the present invention to provide cMUTs in which isolation is provided by spaced isolation areas or posts.

It is a further object of the present invention to provide isolation areas or posts at different locations and with different heights to allow the design and engineering of variation of the capacitance of the cMUT as a function of applied voltage.

There it is provided cMUTs which comprise a bottom electrode, a top membrane electrode, supported space from the bottom electrode by insulating walls and at least one isolation post or area disposed on the top or bottom electrode to limit the deflection of the top electrodes so that it does not contact the bottom electrode and to minimize the number of trapped charges.

BRIEF DESCRIPTION OF THE DRAWINGS

The invention will be more clearly understood from the following description when read in conjunction with the accompanying drawings of which.

DETAILED DESCRIPTION OF THE PREFERRED EMBODIMENTS

Figure 1:
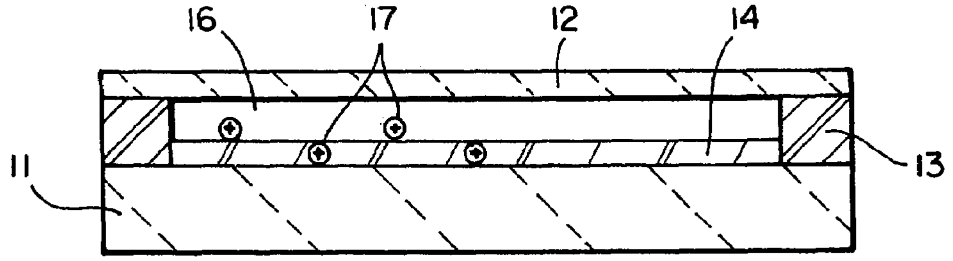
FIG 1 (PRIOR ART)
FIG. 1 is a sectional view of a single cell of a cMUT in accordance with the prior art.
Figure 2:
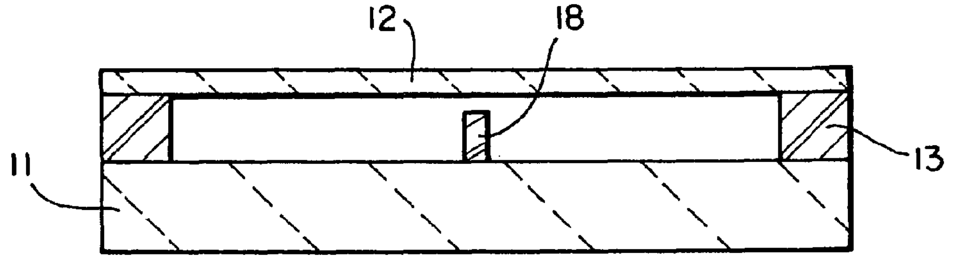
FIG. 2 is a sectional view of a single cell of a cMUT including an isolation post or area in accordance with the present invention.

FIG. 2 illustrates one cell of a cMUT in accordance with the present invention. The same reference numbers have been applied to the like parts. The isolation layer, FIG. 1, is replaced by an isolation post 18 which limits the excursion of the top membrane 12 to prevent shorting while limiting the accumulation of charge. The proper location and height or thickness of the isolation post will prevent shorting between the two electrodes within the device voltage operating range. The isolation posts or areas need to have a thickness such that the electric field across the posts or areas does not result in breakdown of the post materials. Since the post area is very small the charging problem is minimized to negligible value. The location and height of the small post can be designed to the shape of the deflection of the membrane as will presently be described. It is apparent, as will be described, that more than one post or area can be used. It will also be apparent that the isolation area can have any size, shape and height that prevents shorting during operation while reducing the number of trapped charges as compared to a non-patterned isolation layer.

Figure 3A:
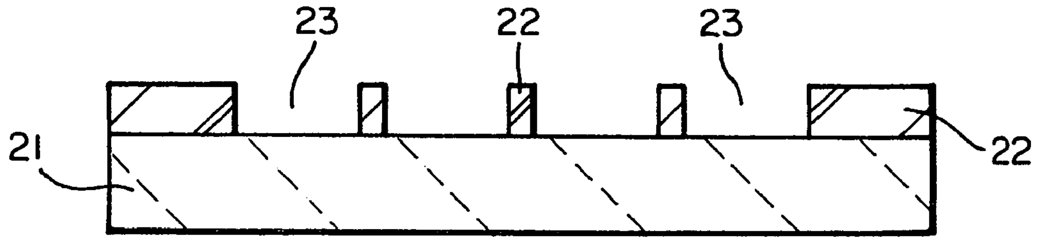
FIG. 3A-3G shows the steps of fabricating a cMUT in accordance with the present invention.
Figure 3B:
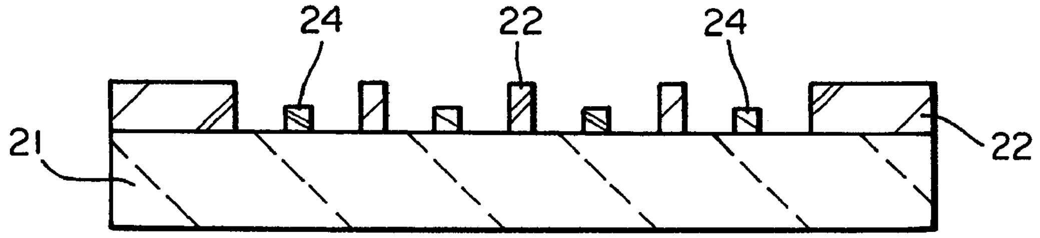
Figure 3C:
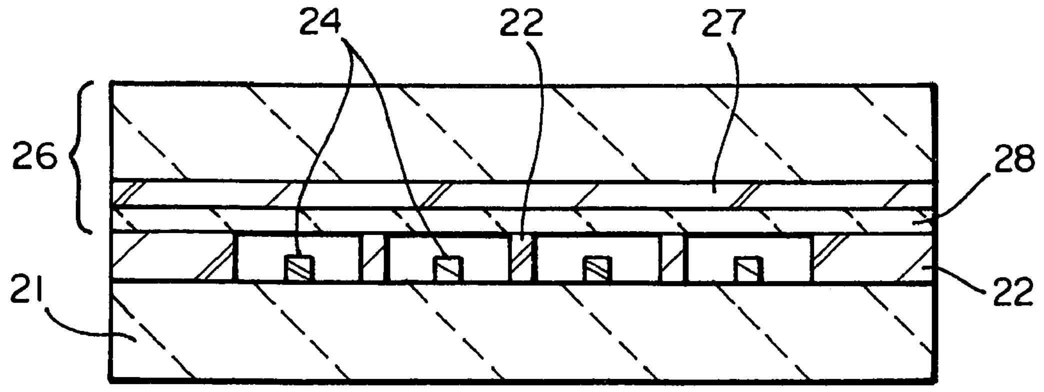
Figure 3D:
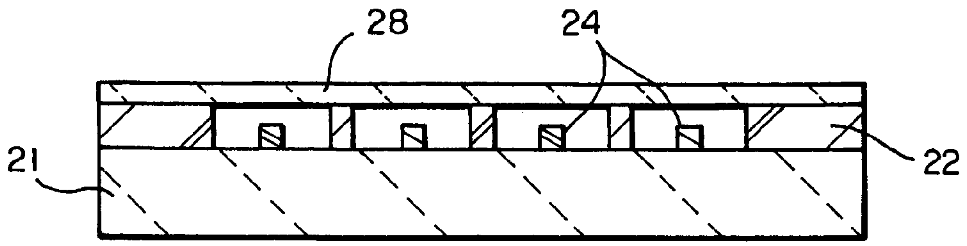
Figure 3E:
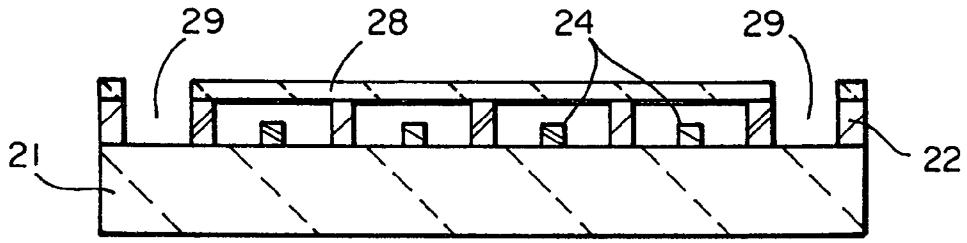
Figure 3F:
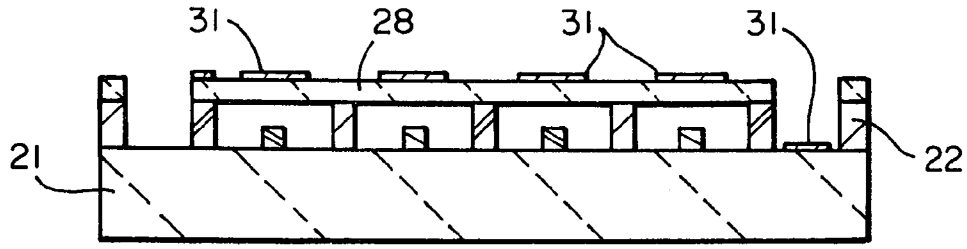
Figure 3G:
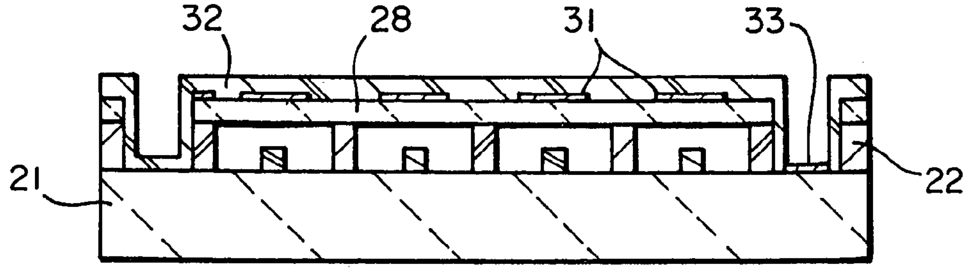

An example of a process for forming cMUT with cells including isolation posts or areas is shown and described with regard to FIGS. 3A-3G. For example, the process may start with an n type silicon wafer 21 FIG. 3A. The wafer can be heavily doped as, for example, with antimony to achieve a low resistance, for example, in the range of 0.008 to 0.020 ohm-centimeters square. Depending on the required electrodes separation of the cMUT one or two different processes form shallow or deep cavities before wafer bonding. When the separation distance between electrodes is less than two micrometers one can use a thermal oxide layer which is etched to form the cavity. A layer 22 of thermal oxide is grown and patterned using convention photolithography and etched to define the wells 23. If the depth of the wells 23 is to be larger than 2 micrometers the wafer is processed by selectively etching the silicon substrate 21 at the bottom of the wells to increase the depth. After the wells have been formed another thermal oxide layer is grown and patterned using conventional photolithography to leave oxide posts or areas 24 at the bottom of the wells, FIG. 3B. It should be understood that the areas can be patterned to have any size and shape. The height of the posts or areas is determined by the thickness of the oxide layer. The wafer with cavities is then bonded to a SOI wafer 26 under vacuum as shown in FIG. 3C. Water bonding can be done with a bonder at approximately $1\times10^{-5}$ microbar vacuum at 150 degrees. The bonded wafers are annealed at 1100 degrees centigrade for two hours. The wafer is ground and etched back through the oxide layer 27 leaving a silicon membrane 28. The active silicon layer 28 on the SOI wafer now constitutes the membrane 28 for the cMUT transducer. The thickness of the active silicon layer 28 becomes the membrane thickness and can be easily controlled. To gain electrical access to the carrier silicon wafer 21 openings 29 in the membrane, silicon and insulating silicon oxide layer are formed by masking and etching. Subsequently a thin film of aluminum 31 is sputtered and patterned to establish a connection to the top electrodes and to the substrate. A thin layer of low temperature oxide 32 then is deposited as a passive layer. Finally, the low temperature oxide layer is patterned and etched to create pads 33 for wire bonding.

Although a silicon substrate and a silicon membrane has been described the same bonding process can be used to fabricate cMUTs with other types of membranes such as silicon nitride, sapphire, diamond, etc. with other substrates such as silicon nitride substrates or other materials and with other insulating isolation materials.

Figure 4:
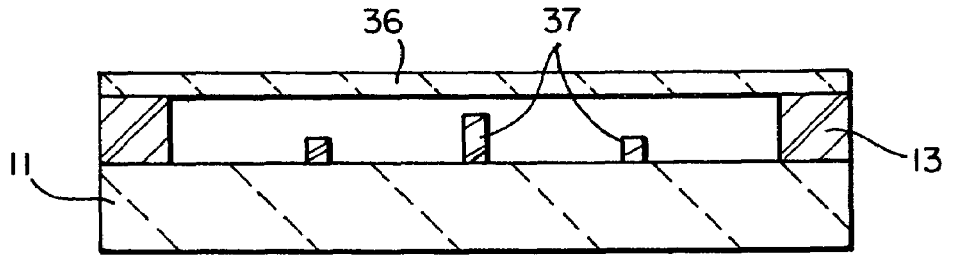
FIG. 4 is a sectional view of a cell of a cMUT with multiple isolation posts.

Referring now to FIG. 4 which illustrates a single cell of a cMUT with a silicon membrane 36 the design and location of the posts 37 is described. The device includes two sets of posts. The location and height of the posts is determined by simulating the membrane deflection under electrostatic force. This is illustrated for the circular cell of FIG. 4. It is apparent that the concept of isolation posts or areas can be applied to any membrane shape in any kind of post design. Furthermore, isolation posts or areas of different sizes, shapes, locations, and heights will allow engineering the variation of capacitance of the cMUT as a function of applied voltages. The location, size and height of the posts or areas can be chosen to optimize the frequency response, or the output pressure and receive sensitivity both before and after contact with the posts or areas.

Figure 5:
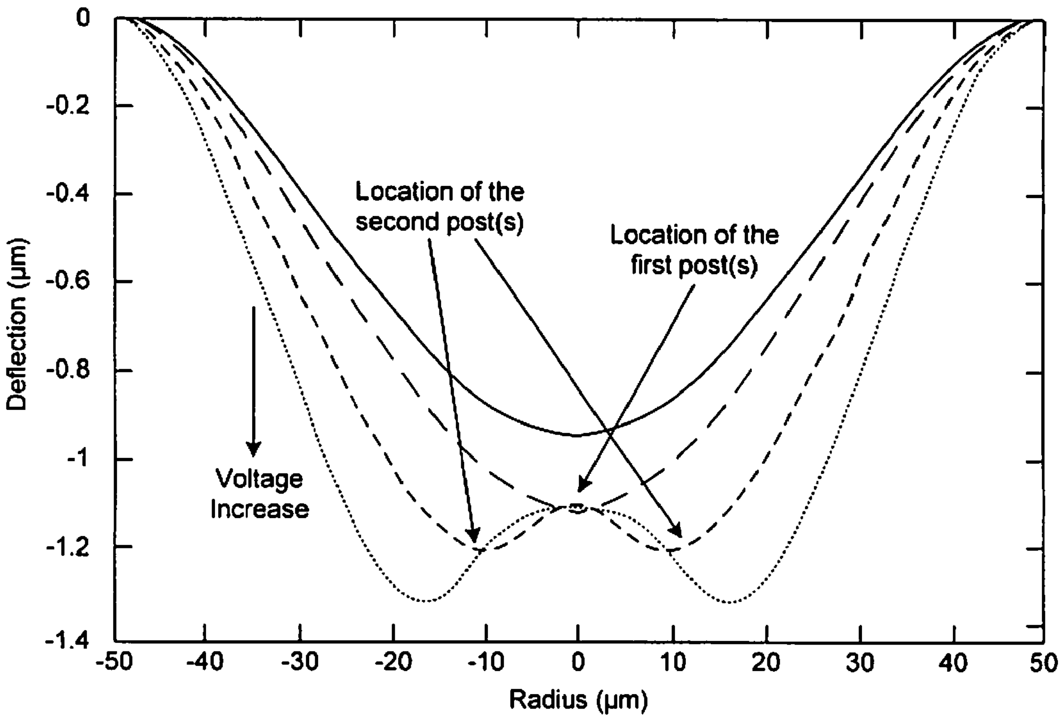
FIG. 5 shows deflection of a membrane as a function of radius with a cMUT such as that shown in FIG. 4.
Figure 6:
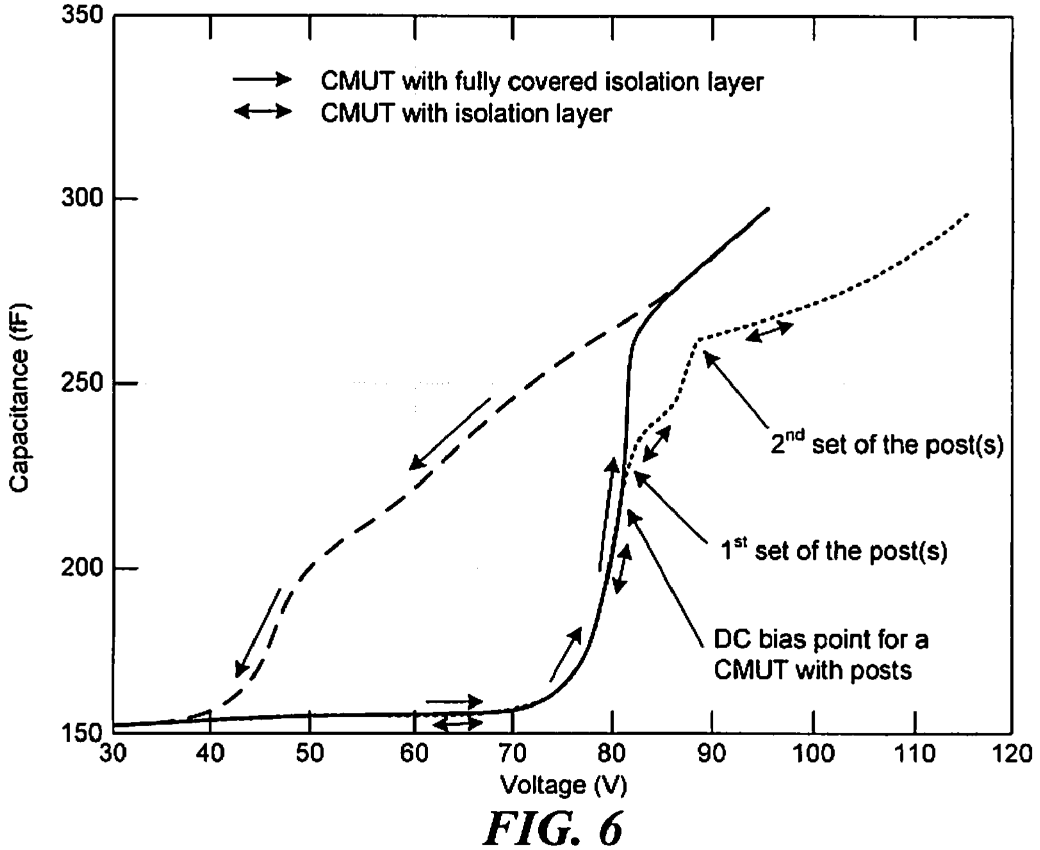
FIG. 6 shows capacitance voltage curves for cMUTs in accordance with the prior art and in accordance with the present invention.

FIG. 5 shows how the location of the first and second set of posts shown in FIG. 4 is determined. FIG. 5 shows the membrane deflection for the cMUT of FIG. 4 and the points of maximum deflection where the post needs to be located. FIG. 6 shows the capacitance as a function of voltage for cMUT's with and without isolation posts. It shows that a cMUT with isolation post(s) can operate over a fuller capacitive range without a pull-in effect by implementing properly designed post(s). Generally the capacitive change for received ultrasonic pressure is very small. Therefore, it is desired for the cMUT to operate very close to its collapse voltage to achieve optimum sensitivity. However, a large AC voltage is needed for a cMUT to transmit the maximum ultrasonic energy to the medium. This makes it almost impossible for the cMUT with a fully covered isolation layer to operate around its collapse voltage reliably due to the pull-in and effect. The monotonic behavior of the CV curve of the new cMUT with isolation posts overcomes the problem. Therefore the cMUT performance can be optimized for both transmission and reception by setting the bias voltage very close to the collapse voltage of the cMUT. The foregoing description illustrates the ability to obtain variations of capacitance and hence displacement as a function of applied voltage.

Figure 7:
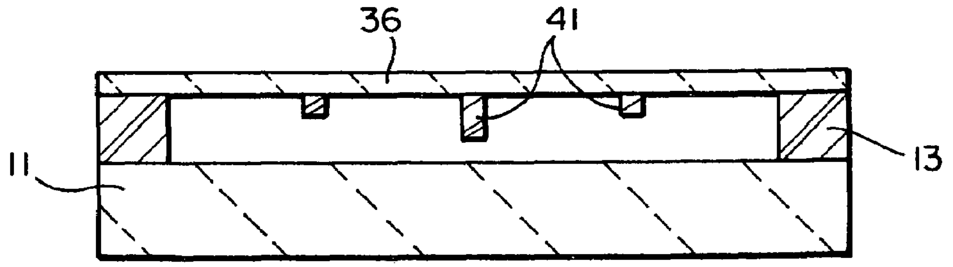
FIG. 7 is a cross sectional view of a cell in accordance with another embodiment of the present invention.

It is apparent that the isolation posts shown in FIG. 4 could be applied to this top electrode membrane 36 prior to bonding and operation would be the same. FIG. 7 illustrates an embodiment of the invention in which the isolation posts 41 are fabricated on the membrane.

Thus there is provided cMUTs in which the shorting of the electrodes is prevented by isolation posts or areas which minimize the accumulation of charge which degrades the reliability and repeatability of device performance. The operation of the cMUT is vastly improved.

What is claimed is:

1. A capacitive ultrasonic transducer comprising at least one cavity defined by a first support electrode, insulating support walls forming with the support electrode wells, and a membrane electrode having a membrane electrode surface area, the membrane electrode supported by the support walls and spaced from the support electrode, characterized in that, at least one isolation post or area of insulating material having a thickness is formed in said at least one cavity, the amount of the membrane electrode surface covered by or disposed adjacent to the at least one isolation post or area being smaller than the full membrane electrode surface area and selected to reduce accumulation of charge between the cost or area and the membrane electrode, and the thickness selected to prevent contact of the membrane electrode to the support electrode during operation of the transducer.

2. A capacitive ultrasonic transducer as in claim 1 in which the support electrode is a low resistance silicon support and the support walls are an oxide, and the membrane is silicon.

3. A capacitive ultrasonic transducer as in claims 1 or 2 in which the at least one isolation post or area is carried by the support electrode.

4. A capacitive ultrasonic transducer as in claims 1 or 2 in which the at least one isolation post or area is carried by the membrane.

5. A capacitive ultrasonic transducer as in claims 1 or 2 in which the at least one isolation post or area is located at a selected location with the size, shape, and height selected to prevent shorting between electrodes and minimize the number of trapped ions.

6. A capacitive ultrasonic transducer as in claim 5 in which the height, shape and location of the at least one isolation post or area is selected so that the membrane comes in contact with the at least one isolation post or area during post contact operation of the transducer.

7. A capacitive ultrasonic transducer as in claim 1 wherein said at least one isolation post or area comprises a plurality of isolation posts or areas at any selected location with height, size and shape which prevents shorting between the electrodes during operation of the transducer and minimizes accumulation of charges.

8. A capacitive ultrasonic transducer comprising:

at least one cavity defined by a support substrate forming a first electrode of said transducer, walls of insulating material on said support and a thin membrane supported by said walls and forming the second electrode of said transducer, said membrane forming said second electrode having a membrane surface area; and at least one post or area of dielectric isolation material having a thickness formed in said at least one cavity, the amount of the membrane surface covered by or disposed adjacent to the at least one post or area being smaller than the full membrane surface area and selected to reduce accumulation of charge between the at least one post or area and the membrane, and the thickness selected for limiting the deflection of said membrane during operation to prevent contact of the membrane with the support substrate during operation of the transducer and to minimize accumulation of charge.

9. A capacitive transducer as in claim 8 in which the membrane material is selected from silicon, silicon nitride, sapphire or diamond.

10. A capacitive ultrasonic transducer as in claims 8 or 9 in which the at least one isolation post or area of dielectric isolation material is a dielectric isolation material.

11. A capacitive ultrasonic transducer as in claim 10 in which the walls of insulating material are a dielectric isolation material.

12. A capacitive ultrasonic transducer as in claims 8 or 9 in which the at least one isolation post or area is formed on the support substrate.

13. A capacitive ultrasonic transducer as in claims 8 or 9 in which the at least one isolation post or area is formed on the membrane.

14. A capacitive ultrasonic transducer as in claims 8 or 9 in which the location of the at least one isolation post or area is chosen to optimize the frequency response of the transducer.

15. A capacitive ultrasonic transducer as in claim 14 in which the size, shape and height of the at least one isolation post or area is further chosen to optimize the frequency response of the transducer.

* * * * *